(12) United States Patent
Fikes

(10) Patent No.: US 9,913,738 B1
(45) Date of Patent: Mar. 13, 2018

(54) CONDITIONAL BRAKING KNEE

(71) Applicant: Raymond Fikes, Mesa, AZ (US)

(72) Inventor: Raymond Fikes, Mesa, AZ (US)

( * ) Notice: Subject to any disclaimer, the term of this patent is extended or adjusted under 35 U.S.C. 154(b) by 0 days.

(21) Appl. No.: 14/278,816

(22) Filed: May 15, 2014

Related U.S. Application Data

(60) Provisional application No. 61/823,821, filed on May 15, 2013.

(51) Int. Cl.
*A61F 2/64* (2006.01)
*A61F 2/68* (2006.01)
(Continued)

(52) U.S. Cl.
CPC .................. *A61F 2/64* (2013.01); *A61F 2/68* (2013.01); *A61F 2/642* (2013.01); *A61F 2/66* (2013.01); *A61F 2002/5003* (2013.01); *A61F 2002/5006* (2013.01); *A61F 2002/5073* (2013.01); *A61F 2002/6818* (2013.01); *A61F 2002/6854* (2013.01); *A61F 2002/6863* (2013.01); *A61F 2002/701* (2013.01); *A61F 2002/704* (2013.01); *A61F 2002/74* (2013.01); *A61F 2002/744* (2013.01); *A61F 2002/745* (2013.01); *A61F 2002/747* (2013.01); *A61F 2002/748* (2013.01)

(58) Field of Classification Search
CPC .... A61F 2/60; A61F 2/64; A61F 2/642; A61F 2/644; A61F 2002/6818; A61F 2002/6854
See application file for complete search history.

(56) References Cited

U.S. PATENT DOCUMENTS 2,559,017 A * 7/1951 Hanson .................. A61F 2/583
188/67
3,723,997 A * 4/1973 Kolman .................. A61F 2/64
623/44
(Continued)

FOREIGN PATENT DOCUMENTS

| DE | 358245 | * | 9/1922 |
| WO | WO 96/41599 | * | 12/1996 |
| WO | WO9733540 A1 | | 9/1997 |

OTHER PUBLICATIONS

Machine Translation of Wilisch German Patent No. 358245 [espacenet machine translation], Nov. 20, 1919.*
(Continued)

*Primary Examiner* — Marcia Watkins
(74) *Attorney, Agent, or Firm* — IPTechLaw

(57) ABSTRACT

A conditional braking knee includes an upper member configured to couple to a prosthetic socket. A braking member couples to the upper member. A lower member couples to the braking member and is configured to rotate with respect to the upper member. A flexion coupler couples to the braking member and is configured to couple to a prosthetic foot. The braking member is configured to prevent a rotation of the upper member relative to the lower member in response to a flexion of the prosthetic foot communicated to the braking member through the flexion coupler. In implementations the braking member is a clamping member rotatably coupled to the upper member with a first axle, the lower member is rotatably coupled to the clamping member with a second axle, and the clamping member prevents a rotation of the upper member relative to the lower member by clamping on the first axle.

12 Claims, 9 Drawing Sheets

(51) Int. Cl.
  *A61F 2/50*    (2006.01)
  *A61F 2/66*    (2006.01)
  *A61F 2/70*    (2006.01)
  *A61F 2/74*    (2006.01)

(56) References Cited

U.S. PATENT DOCUMENTS

| | | |
|---|---|---|
| 5,545,234 A | 8/1996 | Collier |
| D398,058 S | 9/1998 | Collier |
| 5,800,570 A | 9/1998 | Collier |
| 6,355,071 B1 * | 3/2002 | Cheng ................ A61F 2/64 |
| | | 623/45 |
| 7,025,792 B2 | 4/2006 | Collier |
| 7,195,647 B2 * | 3/2007 | Chen ................ A61F 2/644 |
| | | 623/45 |
| 7,468,079 B2 | 12/2008 | Collier |
| 2003/0050712 A1 * | 3/2003 | Shen ................ A61F 2/644 |
| | | 623/45 |
| 2011/0270415 A1 * | 11/2011 | Chen ................ A61F 2/644 |
| | | 623/44 |

OTHER PUBLICATIONS

Machine Translation of Van Der Perre WIPO publication No. WO 96/41599 [google machine translation], Dec. 27, 1996.*
Ottobock Website Images, available online at least as early as May 8, 2014, available online at http://professionals.ottobockus.com/cps/rde/xchg/9b_us_en/hs.xsl/34009.html, last visited May 9, 2014.
Ottobock Product Catalog (Supplement 2012), available online at least as early as May 23, 2013.

* cited by examiner

CONDITIONAL BRAKING KNEE

CROSS REFERENCE TO RELATED APPLICATIONS

This document claims the benefit of the filing date of U.S. Provisional Patent Application 61/823,821, entitled "Conditional Braking Knee" to Raymond Fikes which was filed on May 15, 2013, the disclosure of which is hereby incorporated entirely herein by reference.

BACKGROUND

1. Technical Field

Aspects of this document relate generally to prosthetic knees, legs and feet. Aspects of this document relate generally to braking prosthetic knees.

2. Background Art

Prosthetic knees, legs and feet may be used to help amputees, or persons otherwise missing a limb beginning somewhere above the knee, to ambulate, stand, run, sit, and the like. Prosthetic knees, legs and feet come in a variety of forms. Some prosthetic knees are motorized and include various sensors which help determine the desired position of the knee based on force measurements.

SUMMARY

Implementations of conditional braking knees may include: an upper member configured to couple to a prosthetic socket; a braking member coupled to the upper member; a lower member coupled to the braking member and configured to rotate with respect to the upper member; and a flexion coupler coupled to the braking member and configured to couple to a prosthetic foot; wherein the braking member is configured to prevent a rotation of the upper member relative to the lower member in response to a flexion of the prosthetic foot communicated to the braking member through the flexion coupler.

Implementations of conditional braking knees may include one, all, or any of the following:

The conditional braking knee may further include the prosthetic foot and the prosthetic foot may be coupled to the lower member and to the flexion coupler.

The flexion of the prosthetic foot may be a dorsiflexion.

The flexion of the prosthetic foot may be a plantarflexion.

An extension member may be coupled to the lower member and coupled to the upper member, the extension member configured to one of assist and resist rotation of the upper member relative to the lower member.

The extension member may be coupled to the lower member through a lower axle and may be coupled to the upper member through an upper axle.

The braking member may be configured to prevent a rotation of the upper member relative to the lower member in response to force beyond a specified threshold being applied to the upper member through the prosthetic socket.

The braking member may be configured to brake the conditional braking knee by disallowing a movement of a hydraulic fluid within the conditional braking knee.

Implementations of conditional braking knees may include: an upper member configured to couple to a prosthetic socket; a clamping member rotatably coupled to the upper member with a first axle; a lower member rotatably coupled to the clamping member with a second axle; at least one flexion coupler coupled to the clamping member; and a prosthetic foot coupled to the at least one flexion coupler; wherein the clamping member is configured to prevent a rotation of the upper member relative to the lower member in response to a flexion of the prosthetic foot by clamping on the first axle.

Implementations of conditional braking knees may include one, all, or any of the following:

An extension member may be coupled to the lower member through a lower axle and may be coupled to the upper member through an upper axle, the extension member configured to one of assist and resist rotation of the upper member relative to the lower member.

The extension member may include one of a spring, a pneumatic piston, a hydraulic member, and an electric motor.

The at least one flexion coupler may include a plantarflexion coupler configured to apply a force to the clamping member in response to a plantarflexion of the prosthetic foot.

The force from the plantarflexion coupler may be a downward force.

The at least one flexion coupler may include a dorsiflexion coupler configured to apply a force to the clamping member in response to a dorsiflexion of the prosthetic foot.

The force from the dorsiflexion coupler may be a downward force.

The at least one flexion coupler may include a flexible cable.

The braking member may be configured to prevent a rotation of the upper member relative to the lower member in response to force beyond a specified threshold being applied to the upper member through the prosthetic socket.

Implementations of conditional braking knees may include: an upper member configured to couple to a prosthetic socket; a clamping member rotatably coupled to the upper member with a first axle; a lower member rotatably coupled to the clamping member with a second axle; a plantarflexion coupler coupled to the clamping member; a dorsiflexion coupler coupled to the clamping member; and a prosthetic foot coupled to the plantarflexion coupler and to the dorsiflexion coupler; wherein the plantarflexion coupler is configured to apply a first force to the clamping member in response to a plantarflexion of the prosthetic foot and the clamping member is configured to prevent a rotation of the upper member relative to the lower member in response to the first force by clamping on the first axle; and wherein the dorsiflexion coupler is configured to apply a second force to the clamping member in response to a dorsiflexion of the prosthetic foot and the clamping member is configured to prevent a rotation of the upper member relative to the lower member in response to the second force by clamping on the first axle.

Implementations of conditional braking knees may include one, all, or any of the following:

An extension member may be coupled to the lower member through a lower axle and may be coupled to the upper member through an upper axle, the extension member configured to one of assist and resist rotation of the upper member relative to the lower member.

The braking member may be configured to prevent a rotation of the upper member relative to the lower member in response to force beyond a specified threshold being applied to the upper member through the prosthetic socket.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and.

DESCRIPTION

Figure 1:
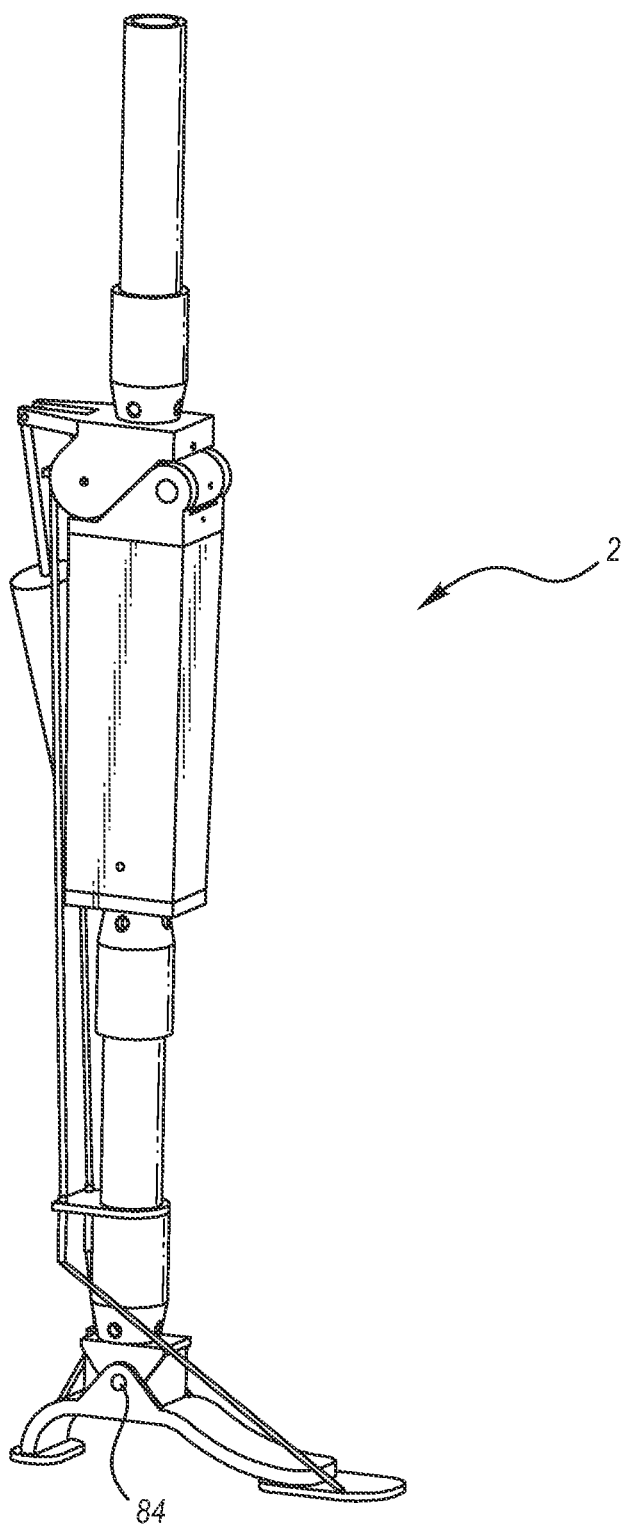
FIG. 1 is a side-front perspective view of an implementation of a conditional braking knee in a non-bent configuration.

This disclosure, its aspects and implementations, are not limited to the specific components, assembly procedures or method elements disclosed herein. Many additional components, assembly procedures and/or method elements known in the art consistent with the intended conditional braking knees and related methods will become apparent for use with particular implementations from this disclosure. Accordingly, for example, although particular implementations are disclosed, such implementations and implementing components may comprise any shape, size, style, type, model, version, measurement, concentration, material, quantity, method element, step, and/or the like as is known in the art for such conditional braking knees and related methods, and implementing components and methods, consistent with the intended operation and methods.

Referring now to FIGS. 1-6B, in implementations a conditional braking knee (CBK) 2 includes an upper member 36 rotatably coupled to a braking member 4. A lower member 52 is also rotatably coupled to the braking member 4. In the implementations shown in FIGS. 1-6B the upper member 36 is coupled to the braking member 4 through a first axle 24 which rotates within a first axle receiver 6 of the braking member 4. In this implementation the braking member 4 is a clamping member 5 that has a cavity 8 which allows the clamping member 5 to, upon an application of sufficient force, clamp down upon the first axle 24 to resist or prevent rotation of the first axle 24. Under the lack of sufficient force the clamping member 5 allows the first axle 24 to move freely within the first axle receiver 6. The transition from free rotation of the first axle 24 to complete inhibition of rotation thereof may be intermediated by varying degrees of freedom of rotation as the friction between the clamping member 5 and the first axle 24 varies due to variations in applied forces. In other implementations the braking mechanism could be configured such that there is either full braking or no braking, without any gradation in braking force.

The upper member 36 is rotatable with respect to the lower member 52. This movement is analogous to the bending of a knee so that, for example, the configuration of FIG. 1 may be considered to be in a "non-bending" or "non-bent" configuration while the configuration of FIG. 2 may be considered to be in a "bending" or "bent" configuration. In other implementations the upper member 36 and lower member 52 could be directly rotatably coupled to one another, for instance they could be hinged together with an axle. In the implementations of FIGS. 1-6B they are indirectly rotatably coupled together by virtue of the upper member 36 being rotatably coupled directly to the braking member 4 through the first axle 24 and the lower member 52 also being rotatably coupled directly to the braking member 4, albeit through a second axle 30 which rotates within a second axle receiver 10 of the braking member 4.

In implementations the braking member 4 could include some mechanism other than a clamping member 5 to resist or prevent rotation of the first axle 24 such as, by non-limiting example, a magnetic element, a hydraulic mechanism, or any other mechanism configured to prevent or resist rotation of the upper member 36 relative to the lower member 52.

The first axle 24 in the implementations of FIGS. 1-6B includes a first aligner 26 which aligns with a second aligner 38 of the upper member 36. In this version the first aligner 26 is a protrusion 28 while the second aligner 38 is a protrusion receiver 40. In other implementations the first aligner 26 could be a protrusion receiver while the second aligner 38 could include a protrusion, or both could include protrusions and protrusion receivers, and the like. The first and second aligners 26, 38 are configured to prevent the upper member 36 from rotating relative to the first axle 24 and, thus, causing the first axle 24 and upper member 36 to instead always rotate together in harmony or unison with one another.

The lower member 52, as indicated, is rotatably coupled directly to the braking member 4 through the second axle 30. The lower member 52 includes a second axle coupler 54 which includes two wings each having a circular through-hole, the through-holes each receiving an end of the second axle 30. In implementations the second axle 30 could be rotatable with respect to the lower member 52, and in other implementations the second axle 30 and lower member 52 may not be rotatable with respect to each other, but the braking member 4 may still be rotatable with respect to the second axle 30 and, thus, with respect to the lower member 52.

Figure 6A:
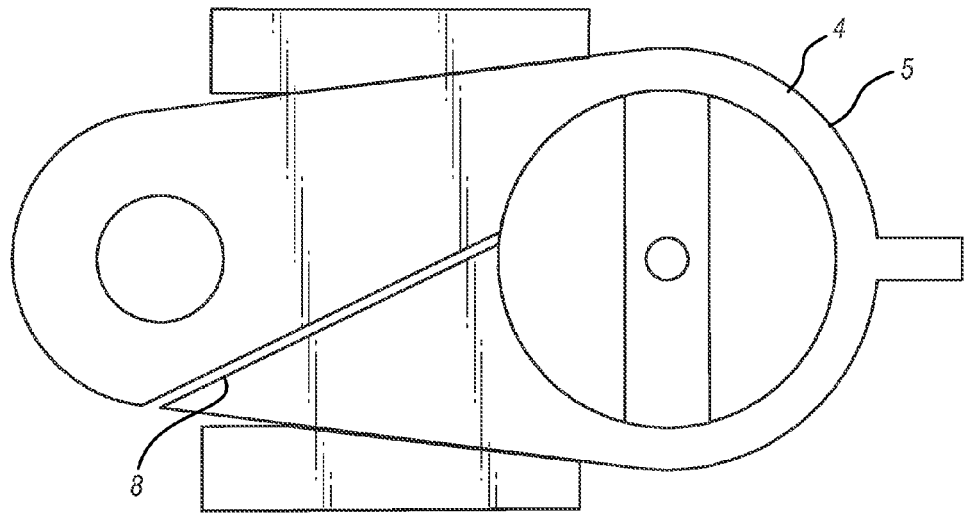
FIG. 6A is a side view of an implementation of some components of the conditional braking knee of FIG. 1 with the conditional braking knee in a non-bent configuration.
Figure 6B:
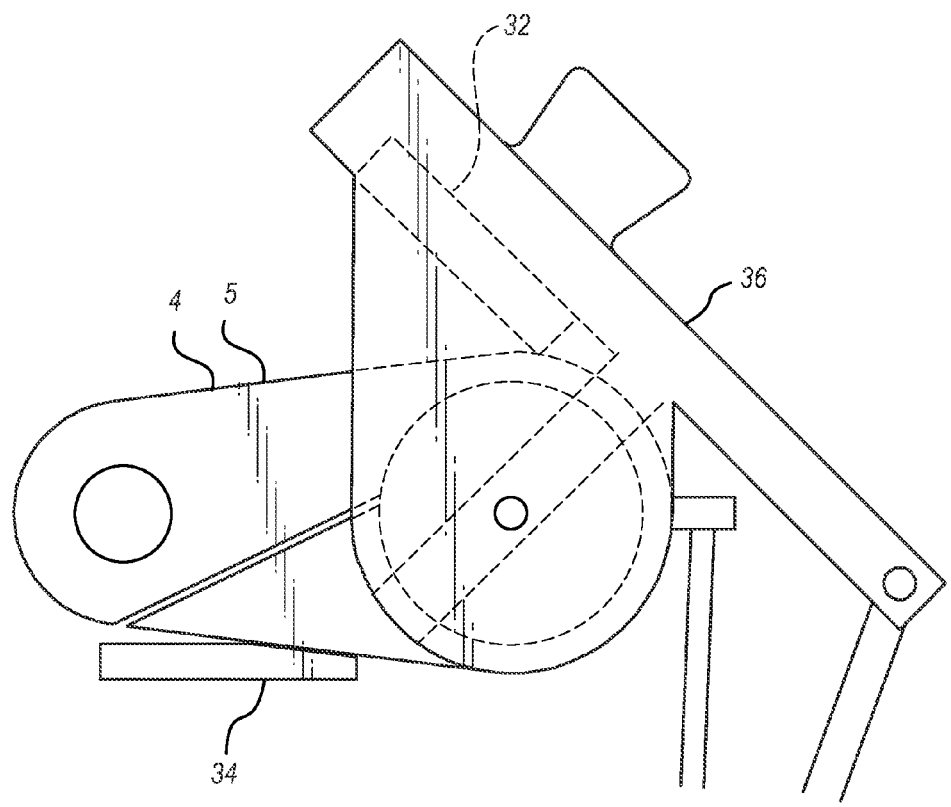
FIG. 6B is a side, see-through view of some components of the conditional braking knee of FIG. 1 with the conditional braking knee in a bent configuration.

Between the clamping member 5 and lower member 52 is a lower wedge 34. Between the clamping member 5 and the upper member 36 is an upper wedge 32. In implementations these wedges may be attached to one or more of the other members. For example in implementations the lower wedge 34 may be attached to either the lower member 52 or the clamping member 5. Likewise, in implementations the upper wedge 32 may be attached to either the clamping member 5 or the upper member 36. In implementations the wedges are configured so that, when the CBK 2 is in a non-bended configuration (as in FIG. 1), a sufficient downward force on the upper member will cause the clamping member 5 to be squeezed between the wedges and, accordingly, will cause the clamping member 5 to clamp down on the first axle 24 to prevent it from rotating with respect to the clamping member 5. In this way the CBK 2 is able to lock, to prevent rotation, when a user is standing upright and, therefore, placing sufficient weight upon the upper member 36 (the weight, naturally, and force, being transferred to the upper member 36 through the socket 110). As can be seen in FIG. 6B, in the implementation shown the upper wedge 32 is attached to the upper member 36.

The braking member 4 includes one or more flexion attachment points configured to receive one or more flexion couplers 97. In the implementations shown in FIGS. 1-6B the braking member 4 includes a plantarflexion attachment point 18 and a dorsiflexion attachment point 12. In other implementations the braking member 4 could include only one or the other. The plantarflexion attachment point 18 in the implementation shown is a protrusion 14 having a through-hole 16, and the dorsiflexion attachment point 12 in the implementation shown is also a protrusion 20 having a through-hole 22. Each flexion attachment point is configured to be coupled to a flexion coupler 97. In other implementations the flexion attachment points could be anything other than protrusions with through-holes so long as they couple the braking member 4 to a flexion coupler 97 such as, by non-limiting example, using a weld, a glue, a friction fit, a screw, and the like. Each flexion coupler 97 is coupled to a prosthetic foot 82 and each flexion coupler 97 allows a flexion of the prosthetic foot 82 in a specified direction to apply a force to the clamping member 5, through the flexion coupler(s) 97 and flexion attachment point(s), to clamp the clamping member 5 down on the first axle 24 and, thereby, prevent rotation of the first axle 24 and effectively "brake" the CBK 2. In this way the CBK 2 is configured to allow a flexion of the prosthetic foot 82 to brake the CBK 2.

In the implementations shown in FIGS. 1-6B the plantarflexion attachment point 18 is coupled to a plantarflexion coupler 102 and the dorsiflexion attachment point 12 is coupled to a dorsiflexion coupler 98. The plantarflexion coupler 102 shown is a first flexible cable 100 and the dorsiflexion coupler 98 shown is a second flexible cable 104. Accordingly, being flexible cables, each flexion coupler 97 is configured to, in general, apply a downward force on the clamping member 5 at the attachment point with the clamping member 5 by tightening the flexion coupler 97 in response to a flexion of the prosthetic foot 82 in a certain direction but, when the flexion is reversed, that same flexion coupler 97 then applies only negligible force to the clamping member 5 by virtue of the general inability of a flexible cable to communicate a significant compressive force along its length.

The upper end of the plantarflexion coupler 102 is coupled to the clamping member 5 at the plantarflexion attachment point 18 and the lower end of the plantarflexion coupler 102 is coupled to the plantarflexion coupler receiver 96 of the prosthetic foot 82. The prosthetic foot 82 includes an upper portion 90 and a lower portion 92 that are coupled together at an ankle axle 84. The upper portion 90 includes a third coupler 86 configured to allow the prosthetic foot 82 to be coupled to a third coupler receiver 78. In the implementation shown the third coupler 86 is an endoskeletal pyramid 88, though in other implementations it could include other coupler types. The ankle axle 84 allows the upper portion 90 and lower portion 92 to rotate with respect to one another in plantarflexion and in dorsiflexion of the prosthetic foot 82. Dorsiflexion of the prosthetic foot 82 shown in the drawings is rotation of the toe end of the prosthetic foot 82 upwards (away from the ground surface) relative to the ankle axle 84 and, correspondingly, rotation of the heel end in a downwards direction (toward the ground surface) relative to the ankle axle 84. Plantarflexion of the prosthetic foot 82 shown in the drawings is rotation of the toe end of the prosthetic foot 82 in a downwards direction relative to the ankle axle 84 and, correspondingly, rotation of the heel end in an upwards direction relative to the ankle axle 84.

In other implementations a different prosthetic foot than that shown in the drawings could be used. By non-limiting example, in other implementations the heel end of the foot and the toe end of the foot could move independent of one another instead and/or an ankle axle may or may not be included. Accordingly, whichever version of a prosthetic foot is used in the CBK 2, dorsiflexion may generically be referred to as movement of the toe end of the prosthetic foot in an upwards direction and plantarflexion may generically be referred to as movement of the heel end of the prosthetic foot in an upwards direction.

Referring still to FIGS. 1-6B, as indicated above the upper end of the plantarflexion coupler 102 is coupled to the plantarflexion attachment point 18 of the clamping member 5 and the lower end of the plantarflexion coupler 102 is coupled to the plantarflexion coupler receiver 96 of the prosthetic foot 82, the plantarflexion coupler receiver 96 being located proximate the toe end of the prosthetic foot 82 (and, in the implementation shown, also being located between the ankle axle 84 and the toe end of the prosthetic foot 82). The upper end of the dorsiflexion coupler 98 couples to the dorsiflexion attachment point 12 of the clamping member 5 and the lower end of the dorsiflexion coupler 98 couples to the dorsiflexion coupler receiver 94 of the prosthetic foot 82, the dorsiflexion coupler receiver 94 being located proximate the heel end of the prosthetic foot 82 (and, in the implementation shown, also being located between the ankle axle 84 and the heel end of the prosthetic foot 82).

When the lower portion 92 of the prosthetic foot 82 is rotated about the ankle axle 84 towards a dorsiflexion configuration the dorsiflexion coupler 98, being a first flexible cable 100, tightens and thus pulls down on the clamping member 5 at the dorsiflexion attachment point 12, thus braking the CBK 2. At the same time, in dorsiflexion of the prosthetic foot 82 the plantarflexion coupler 102, being a second flexible cable 104, exerts negligible force on the plantarflexion attachment point 18. When the lower portion 92 of the prosthetic foot 82 is rotated about the ankle axle 84 towards a plantarflexion configuration the plantarflexion coupler 102, being a second flexible cable 104, tightens and thus pulls down on the clamping member 5 at the plantarflexion attachment point 18, thus braking the CBK 2. At the same time, in plantarflexion of the prosthetic foot 82 the dorsiflexion coupler 98, being a first flexible cable 100, exerts negligible force on the dorsiflexion attachment point 12. In this way the CBK 2 can be caused to brake during both a dorsiflexion and a plantarflexion of the prosthetic foot 82.

Thus, by non-limiting example, when a user is walking using the CBK2, if the user desires to brake the CBK 2, the user may place either the toe end or the heel end of the prosthetic foot 82 on a surface and exert a force thereon by applying the user's weight and, thereby, may brake the CBK 2. This may be useful, by non-limiting example, when a user is walking, running, attempting to climb or descend stairs, and the like, and the user needs to be able to brake the CBK 2 at some desired point in order to allow the user sufficient support to continue to walk, run, climb or descend without having to bend the CBK 2 at an awkward angle or risk falling if the CBK 2 fails to brake.

As indicated above, in various implementations the CBK 2 also has a braking mechanism that brakes the CBK 2 when sufficient force (such as simply the weight of a user) is transmitted downwards when the user is in a standing position, by squeezing the clamping member 5 between the upper wedge 32 and lower wedge 34 (and, resultantly, resisting or preventing rotation of the first axle 24 relative to the clamping member 5) when a user is standing upright. This braking mechanism releases when the weight or force is released so that, for example, when a user moves the leg in ambulation to a position where the prosthetic foot 82 is no longer resting on a surface, or when the user otherwise is in a position where the user's weight is not causing the clamping member 5 to be squeezed between the upper wedge 32 and lower wedge 34 (such as in a sitting position or when the user otherwise shifts weight off of the upper member 36), the first axle 24 will be free to rotate relative to the clamping member 5 (assuming the dorsiflexion and plantarflexion braking mechanisms are not braking the clamping member 5). Through the upper wedge 32 and lower wedge 34 it may be understood that this braking mechanism, from the weight of the user, may be operative even when the CBK 2 is not in a fully extended configuration (or, in other words, when the CBK 2 is in a somewhat bent configuration), though beyond some position of bending the upper wedge 32 and lower wedge 34 will no longer be able to sufficiently squeeze the clamping member 5 to cause this type of braking to be effective (in the bended configuration of FIG. 6B, for instance, the weight of the user may no longer be able to effectively brake the CBK 2).

Thus this standing braking mechanism, when used alone, may cause a user difficulty in certain circumstances. By non-limiting example, when a user is ascending a staircase, if the user is ascending with a prosthetic leg as the leg in front, if the prosthetic leg has only this type of braking mechanism the user may have difficulty getting the prosthetic leg to a sufficiently extended (non-bent) configuration in order to operate the braking mechanism to allow the user to then place weight on the front leg to bring the lower leg up. Likewise, if a user is descending a staircase similar issues may occur. Such issues may also be experienced whether a user is descending or ascending, and whether the prosthetic leg is the leg in front or the leg in back. With the CBK 2 the user is allowed two other braking mechanisms to assist the user to brake the CBK 2 at a desired position. Thus, in walking, running, standing, ascending, descending, and the like, the user at any point may place the toe end or heel end of the prosthetic foot 82 on a surface and allow the user's weight to cause plantarflexion or dorsiflexion of the prosthetic foot 82 and, accordingly, brake the CBK 2 at that position.

Thus, the CBK 2 has three braking mechanisms: a first braking mechanism whereby the CBK 2 brakes in response to sufficient weight or force of a user in a standing position when the CBK 2 is generally in a non-bent (or is more towards a non-bent) configuration; a plantarflexion braking mechanism operated by plantarflexion of the prosthetic foot 82, and; a dorsiflexion braking mechanism operated by dorsiflexion of the prosthetic foot 82.

Figure 2:
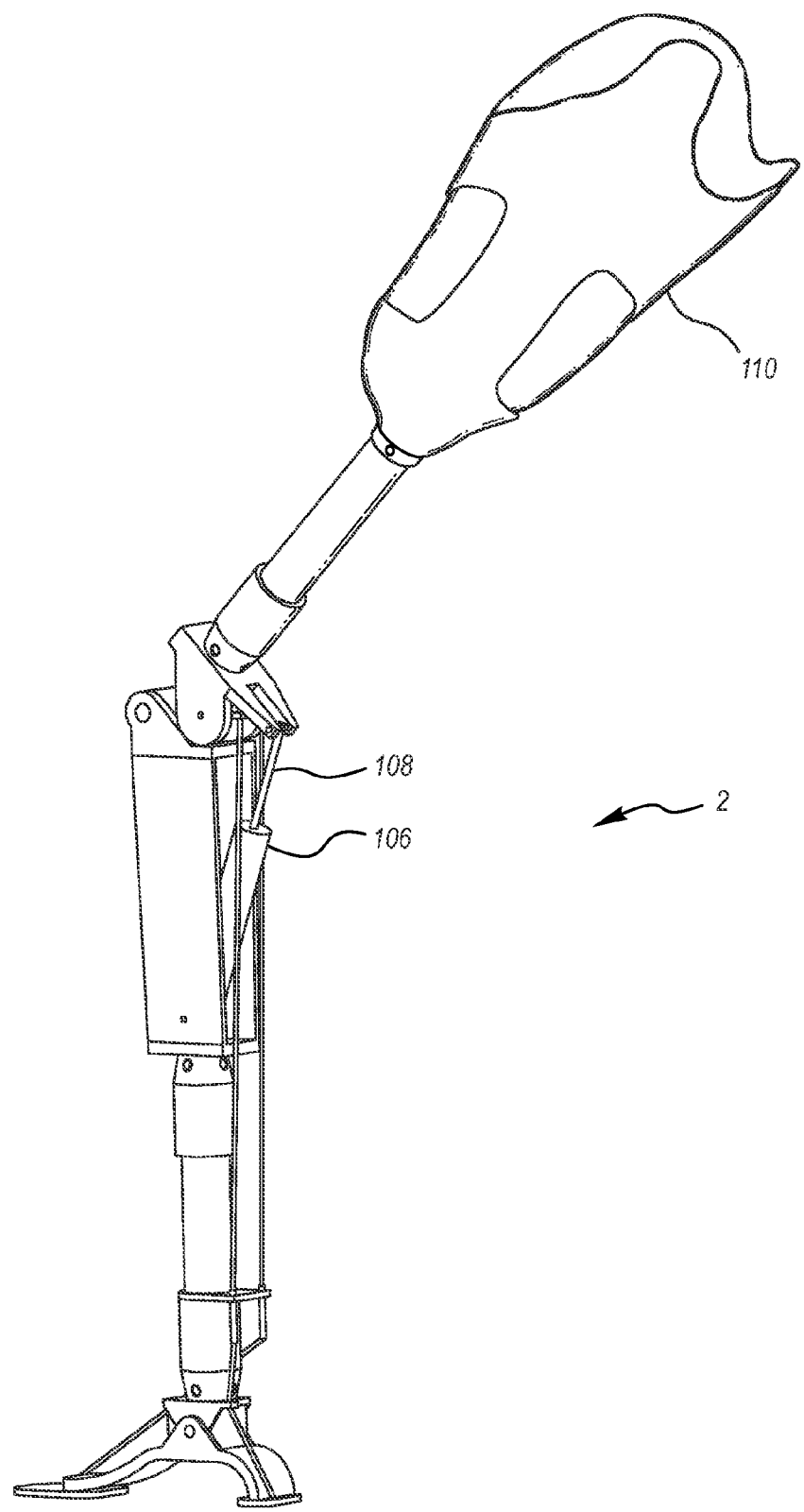
FIG. 2 is a side-rear perspective view of the conditional braking knee of FIG. 1 in a bent configuration and with a socket coupled thereto.
Figure 3:
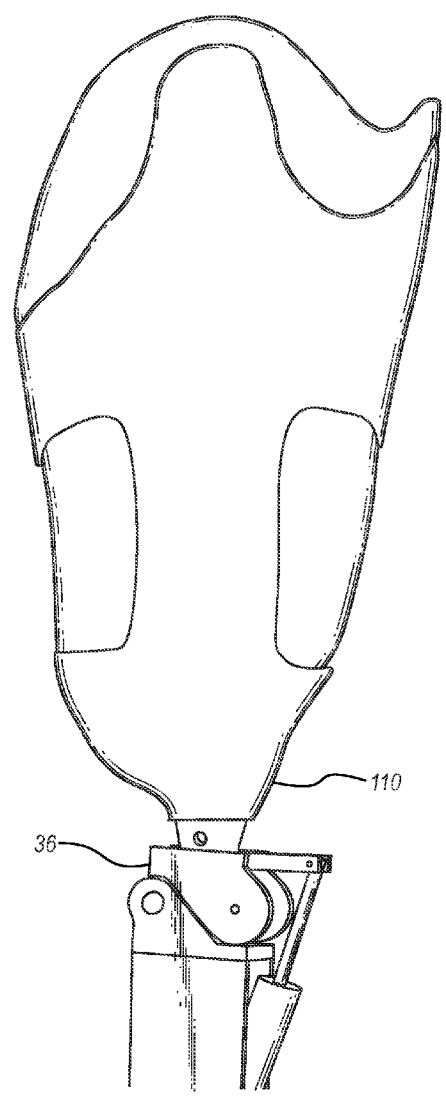
FIG. 3 is a side-rear view of some components of the conditional braking knee of FIG. 1 with a socket coupled thereto.
Figure 4:
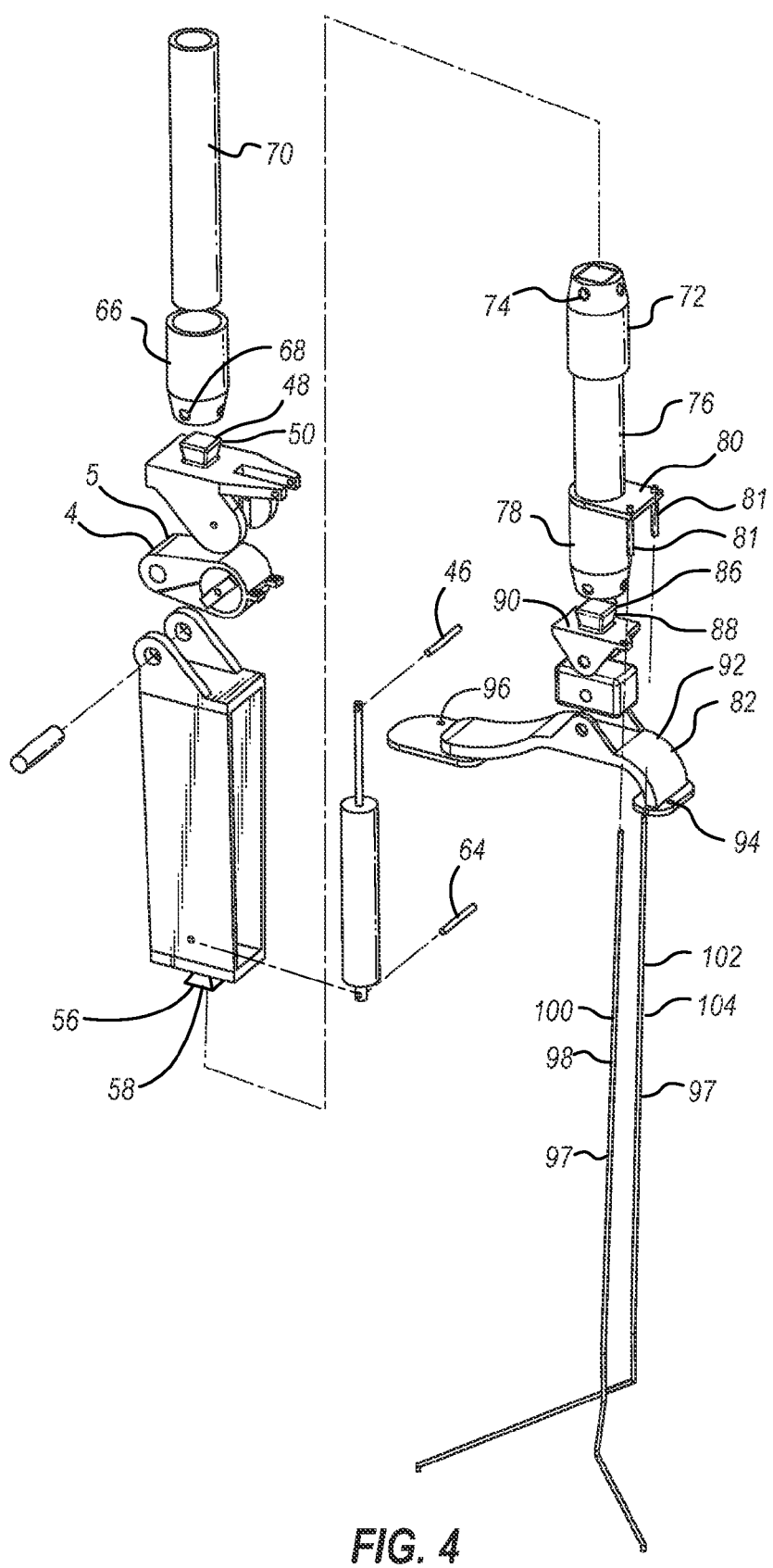
FIG. 4 is an exploded view of the conditional braking knee of FIG. 1.
Figure 5:
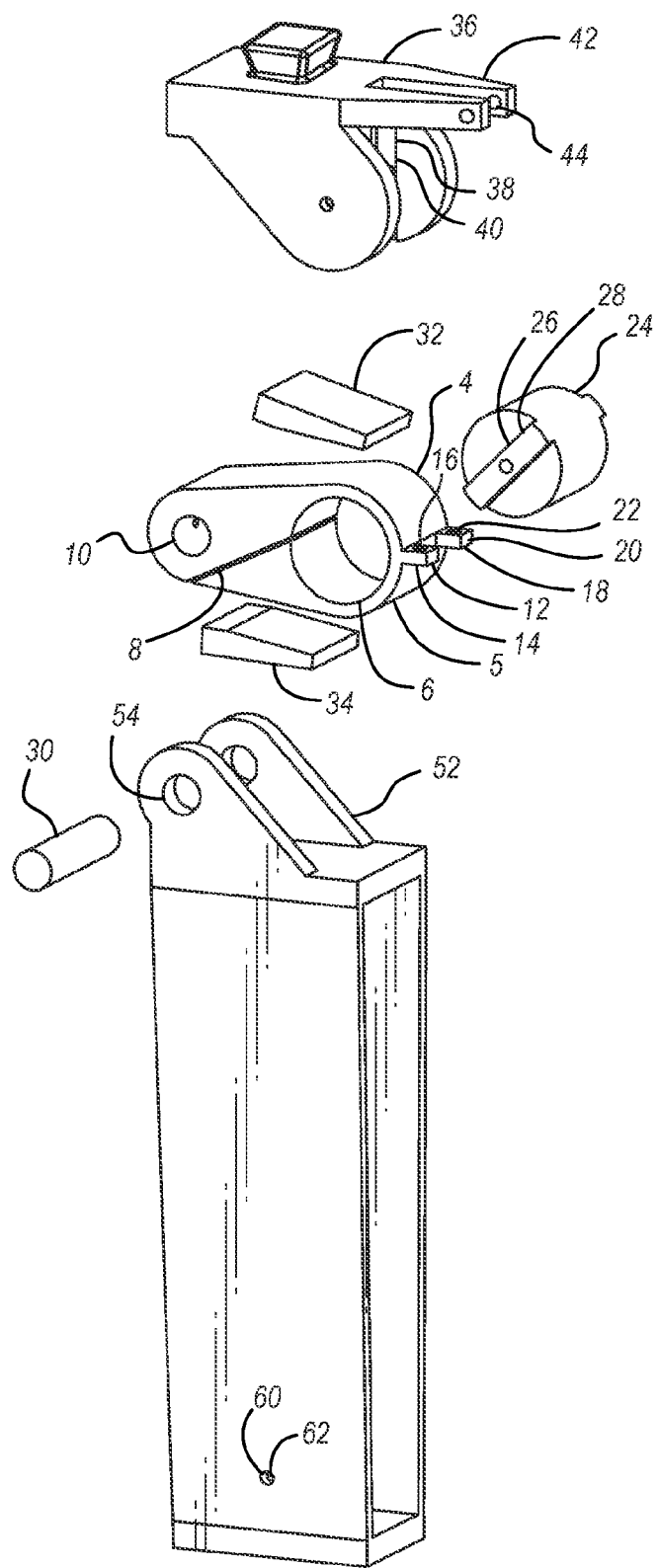
FIG. 5 is an exploded view of some components of the conditional braking knee of FIG. 1.

Referring still to FIGS. 1-6B, the CBK 2 includes a first coupler 48 above the knee joint which, in the implementation shown, is an endoskeletal pyramid 50, though in other implementations it could have any other coupling device. A first coupler receiver 66 may be coupled to the first coupler 48. The first coupler receiver 66 has a plurality of screw holes 68, each of which receives a threaded screw to tighten around the first coupler 48 to hold the first coupler receiver 66 and first coupler 48 in a tight, fixed configuration relative to one another. In implementations a first vertical member 70 is included which itself may, in implementations, have a coupler at its upper end such as, by non-limiting example, an endoskeletal pyramid, such as for the receipt of a socket 110 (which socket 110, in implementations, may have at its lower end a coupler receiver with a plurality of screw holes similar to the first coupler receiver 66, for attachment to the endoskeletal pyramid or other coupler). As shown in FIG. 3, in implementations the first vertical member 70 could be omitted and the socket 110 could be coupled directly to the first coupler 48 of the upper member 36. The socket 110 is configured to receive a residual limb of a user.

The lower member 52 has a second coupler 56 which, in the implementation shown, is an endoskeletal pyramid 58, though in other implementations, it could have any other configuration. The second coupler 56 is configured to coupler to the second coupler receiver 72 which includes a plurality of screw holes 74 configured to receive threaded screws to tighten the second coupler 56 to the second coupler receiver 72 in a tight, fixed configuration. An upper end of a second vertical member 76 couples to the second coupler receiver 72 and a lower end of the second vertical member couples to the third coupler receiver 78. The third coupler receiver 78 also includes a plurality of screw holes configure to receive threaded screws to tighten the third coupler receiver 78 and the third coupler 86 in a tight, fixed configuration relative to one another. In implementations each of the coupler receivers disclosed herein may include four screw holes, each screw hole configured to allow a screw to tighten against one of four faces of an endoskeletal pyramid.

A support 80 is coupled to the second vertical member 76 and/or to the third coupler receiver 78 and has a pair of flexion coupler holders 81 which in the implementation shown are hollow tubes, though in other implementations they could simply be through-holes or slots in the support 80 or any other element. The flexion coupler holders 81 hold the flexion couplers 97 generally at a desired location while allowing the flexion couplers 97 freedom of movement along their longest length. Thus, the support 80 may be used to route or direct the flexion couplers 97 to desired locations such as, by non-limiting example, to have the flexion couplers 97 less likely to interfere with other components of the CBK 2 or to otherwise be placed at desirable locations to assist in their performance. In implementations the support 80 may be excluded, while in other implementations more than one support 80 could be included such as 2, 3, 4, 5, 6, or more supports 80. In the implementation shown the support 80 has a through-hole that receives the second vertical member 76. In implementations the support 80 could be fixedly secured to the second vertical member 76, the third coupler receiver 78, or some other element, such as with a weld, a friction fit, screws, a glue, and the like.

Referring still to FIGS. 1-6B, the CBK 2 includes an extension member 106 which includes a piston 108. The lower end of the extension member 106 couples to a lower extension coupler 60 of the lower member 52. In the implementation shown the lower extension coupler 60 is a lower axle receiver 62 configured to receive a lower axle 64 which sits in a through-hole at a lower end of the extension member 106. In other implementations some configuration other than an axle coupling mechanism could be used to couple the extension member 106 to the lower member 52 such as, by non-limiting example, a friction fit, a glue, a weld, a slot that the lower end of the extension member 106 slides in, a flexible member which allows the extension member 106 to rotate relative to the lower member 52 by virtue of flexion of the flexible member, and so forth. In general, the extension member 106 may be fixedly attached to one of the upper member 36 and lower member 52 so long as it is in some way movable with respect to the other. In the implementation shown the extension member 106 is rotatably coupled to both the upper member 36 and lower member 52 through axles. The upper member 36 has an upper extension coupler 42 configured to couple to an upper end of the extension member 106. In the implementation shown the upper extension coupler 42 includes an upper axle receiver 44 configured to receive an upper axle 46 that sits in a through-hole of the piston 108, though in other implementations the upper extension coupler 42 could have any other configuration as is described above with respect to the lower extension coupler 60.

The extension member 106 is configured to assist and/or resist rotation of the upper member 36 relative to the lower member 52. By non-limiting example, in implementations the extension member 106 is a pneumatic piston mechanism that resists extension and/or bending of the CBK 2 to some degree. In implementations the extension member 106 could be configured to resist either only bending or only extending of the CBK 2. In implementations the extension member 106 could bias the CBK 2 towards a certain configuration. For example in implementations the extension member 106 could bias the CBK 2 towards an extended configuration. In other implementations the extension member 106 could bias the CBK 2 towards a bended configuration. In implementations the extension member 106 may be configured to rotate the upper member 36 relative to the lower member 52. By non-limiting example, in implementations the extension member 106 may include one or more of a motor, a spring, a pneumatic controlled piston, a hydraulic mechanism, or the like, that is actuated in response to some event to, for instance, extend or bend the CBK 2 on demand. The extension member 106 may, for instance, include a motor and may be configured to extend the CBK 2 upon the pressing of a button, or in response to some other event, to help a user stand from a sitting position by extending the CBK 2 automatically using the motor.

In implementations the dorsiflexion coupler 98 and plantarflexion coupler 102 could comprise, instead of flexible cables, rigid push rods that provide an upward force to the braking member 4, this upward force being configured to cause the clamping member 5 to brake, or the upward force otherwise being converted to a downward force through mechanical or other mechanisms to cause the clamping member 5 to brake the CBK 2.

Figure 7:
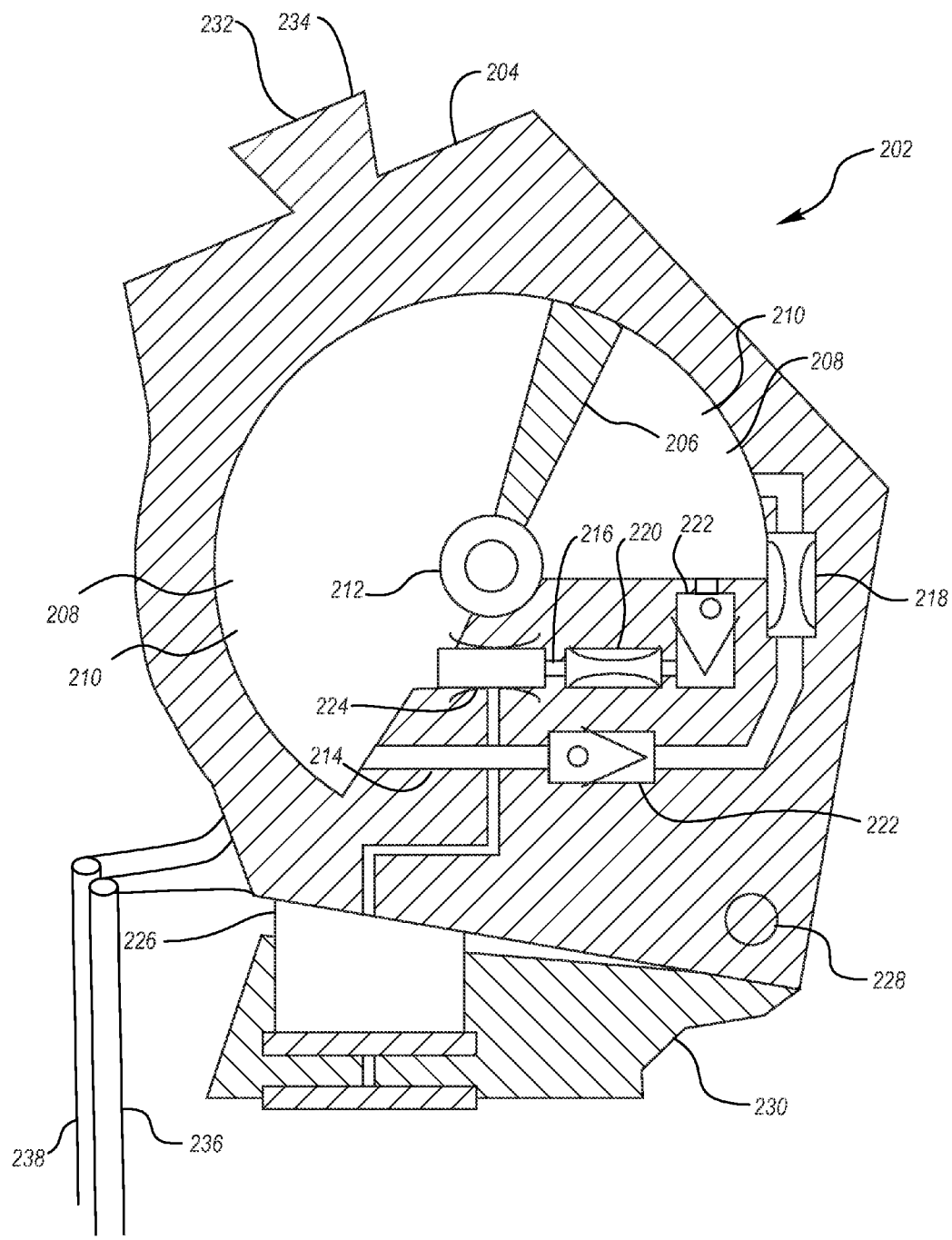
FIG. 7 is a side, cross-section view of some components of another implementation of a conditional braking/yielding knee.

Referring now to FIG. 7, some components of a conditional braking knee (CBK) 202 are shown. Other components of other conditional braking knees and/or conditional yielding knees could be included in the CBK 202, and only the portion of the CBK 202 that is close to the knee joint is shown in FIG. 7.

The CBK 202 includes a first knee member 204 which includes a circular cavity 210 filled with a hydraulic fluid 208. A piston member 206 resides in the circular cavity 210 in a sealed but rotatable configuration between an outer wall of the circular cavity 210 and a first axle 212 or an inner wall proximate the first axle 212—the piston member 206 rotatable about the first axle 212. The piston member 206 in implementations may be coupled to a second knee member which mates with the first knee member in a sealed but rotatable configuration such that the bending of the CBK 202 through the rotation of the first knee member 204 relative to the second knee member causes the piston member 206 to move in the circular cavity 210. When the piston member 206 moves in either direction/rotation the hydraulic fluid 208 is forced through either the first channel 214 or second channel 216.

If the piston member 206 rotates counter-clockwise, by virtue of the first knee member 204 rotating relative to the second knee member, then some of the hydraulic fluid 208 in the circular cavity 210 that is counter-clockwise to the piston member 206 will be forced into the first channel 214, past the check valve 222, past the swing extension valve 218 (assuming that valve is open) and into the portion of the circular cavity 210 that is clockwise to the piston member 206. Naturally, if the swing extension valve 218 is partially or fully closed then the hydraulic fluid 208 will move more slowly, or will not be able to move, in this direction, the piston member 206 will be slowed or prevented from rotating counter-clockwise in the circular cavity 210 and, accordingly, assuming the second knee member is fixedly coupled to the piston member 206 such that the two are not movable relative to one another, the CBK 202 will then be slowed or stopped in this rotation.

If the piston member 206 rotates clockwise, by virtue of the first knee member 204 rotating relative to the second knee member, then some of the hydraulic fluid 208 in the circular cavity 210 that is clockwise to the piston member 206 will be forced into the second channel 216, past the check valve 222, past the swing flexion valve 220 (assuming that valve is open), past the weight valve 224 (assuming that valve is open), and into the portion of the circular cavity 210 that is counter-clockwise to the piston member 206. Naturally, if either or both of the swing flexion valve 220 and/or weight valve 224 are partially or fully closed then the hydraulic fluid 208 will move more slowly, or will not be able to move, in this direction, the piston member 206 will be slowed or prevented from rotating clockwise in the circular cavity 210 and, accordingly, assuming the second knee member is fixedly coupled to the piston member 206 such that the two are not movable relative to one another, the CBK 202 will then be slowed or stopped in this rotation.

In the implementation shown the circular cavity 210 and both the first channel 214 and second channel 216 are generally always completely, or substantially completely, filled with the hydraulic fluid 208.

The check valves 222 are one-way valves that resist or prevent the hydraulic fluid 208 from flowing opposite the directions explained above in the channels. The swing extension valve 218 and swing flexion valve 220 may be partially or fully closed in response to one or more events in order to slow or prevent flow of the hydraulic fluid 208 through the respective channel in order to slow or prevent the rotation or bending of the CBK 202 (in other words, to effectively slow down or lock the bending or extension of CBK 202). The swing extension valve 218 and swing flexion valve 220 may each be operated with a mechanical element, such as a push rod or, as described above with respect to the CBK 2, with flexible cables. As such, they may be configured to operate in response to a dorsiflexion and/or a plantarflexion of a prosthetic foot coupled thereto. In implementations the hydraulic resistance may be increased gradually with increased pressure from a cable or rod, such as through plantarflexion or dorsiflexion, until full braking is achieved.

In implementations one or both of the swing extension valve 218 and swing flexion valve 220 may be configured to not fully close (i.e., to not fully prevent flow of the hydraulic fluid 208 therethrough) when activated in order to provide only hydraulic resistance instead of full braking of the CBK 202. For example, in implementations a dorsiflexion cable or push rod may be configured to only trigger hydraulic resistance and a plantarflexion cable or push rod may be configured to trigger a full braking of the CBK 202. The hydraulic resistance may be configured to increase or decrease within prescribed limits as the force from a push rod or cable is increased or decreased. Either or both of the swing extension valve 218 and swing flexion valve 220 could also be configured to be operated with non-mechanical mechanisms, such as by receiving an electrical input from a prosthetic foot in response to plantarflexion or dorsiflexion and, accordingly, sending a signal to an electric or electro-mechanic element of the respective valve in order to open or close the valve.

A lower knee member 230 is rotatably coupled to the first knee member 204 through a second axle 228. A weight valve controller 226 is configured to active the weight valve 224 in response to rotation of the lower knee member 230 towards the first knee member 204 in response to sufficient downward force on the CBK 202 while in a standing configuration. For instance, the weight valve controller may be a fluid container that is configured to force fluid upwards to fill a diaphragm of the weight valve 224 to close or approach closure of the weight valve 224 to slow or brake the CBK 202. In implementations the weight valve 224 may also be activated at heel strike of a prosthetic foot by also causing the lower knee member 230 to rotate towards the first knee member 204 about the second axle 228. In implementations the weight valve controller could instead operate electronically by receiving an electrical in put in response to a rotation of the lower knee member 230 relative to the first knee member 204 and sending a signal to an electrical or electro-mechanical element of the weight valve 224 to partially or fully close it.

At a top of the first knee member 204 is a first coupler 232 to couple the CBK 202 to a prosthetic socket and, accordingly, to a residual limb of a user. In the implementation shown the first coupler 232 is an endoskeletal pyramid 234, though in other implementations the first coupler 232 could comprise any other configuration. In implementations the CBK 212 will also have a coupler at its lower end similar to the CBK 2 and other conditional braking knees disclosed herein.

In implementations the CBK 202 includes a plantarflexion coupler 236 and/or a dorsiflexion coupler 238 coupled to the lower knee member 230 as shown in FIG. 7, allowing plantarflexion and/or dorsiflexion of a prosthetic foot to operate the weight valve 224, by affecting the weight valve controller 226, to brake the CBK 202. In such an implementation the swing extension valve 218 and/or the swing flexion valve 220 may be omitted or, in implementations, they may be valves which are adjusted to some level to cause a desired fluid resistance during normal swinging of the knee but they may otherwise be unaffected by dorsiflexion and/or plantarflexion of the prosthetic foot. In implementations the addition of a dorsiflexion braking mechanism (such as by coupling a dorsiflexion coupler 238 at the location shown in FIG. 7 where it pulls down on the first knee member 204 to affect the weight valve controller 226) may improve over a conventional hydraulic braking knee or hydraulic yielding knee since, with some conventional hydraulic braking knees or hydraulic yielding knees, the weight activated braking mechanism is activated at heel strike but not at toe strike. With the implementation shown in FIG. 7 the weight activated braking mechanism may be activated at toe strike as well through the use of a dorsiflexion coupler 238. Additionally, the use of a plantarflexion coupler 236 with the implementation of FIG. 7 may allow a user to brake the knee with the heel through plantarflexion in positions wherein the weight activated braking mechanism would not normally be activated, such as when the knee is bent enough so that the user's weight is not pressing downwardly enough on the weight valve controller 226 (due to its being at an angle to the direction of the weight), such as while ascending or descending stairs, or the like.

Figure 8:
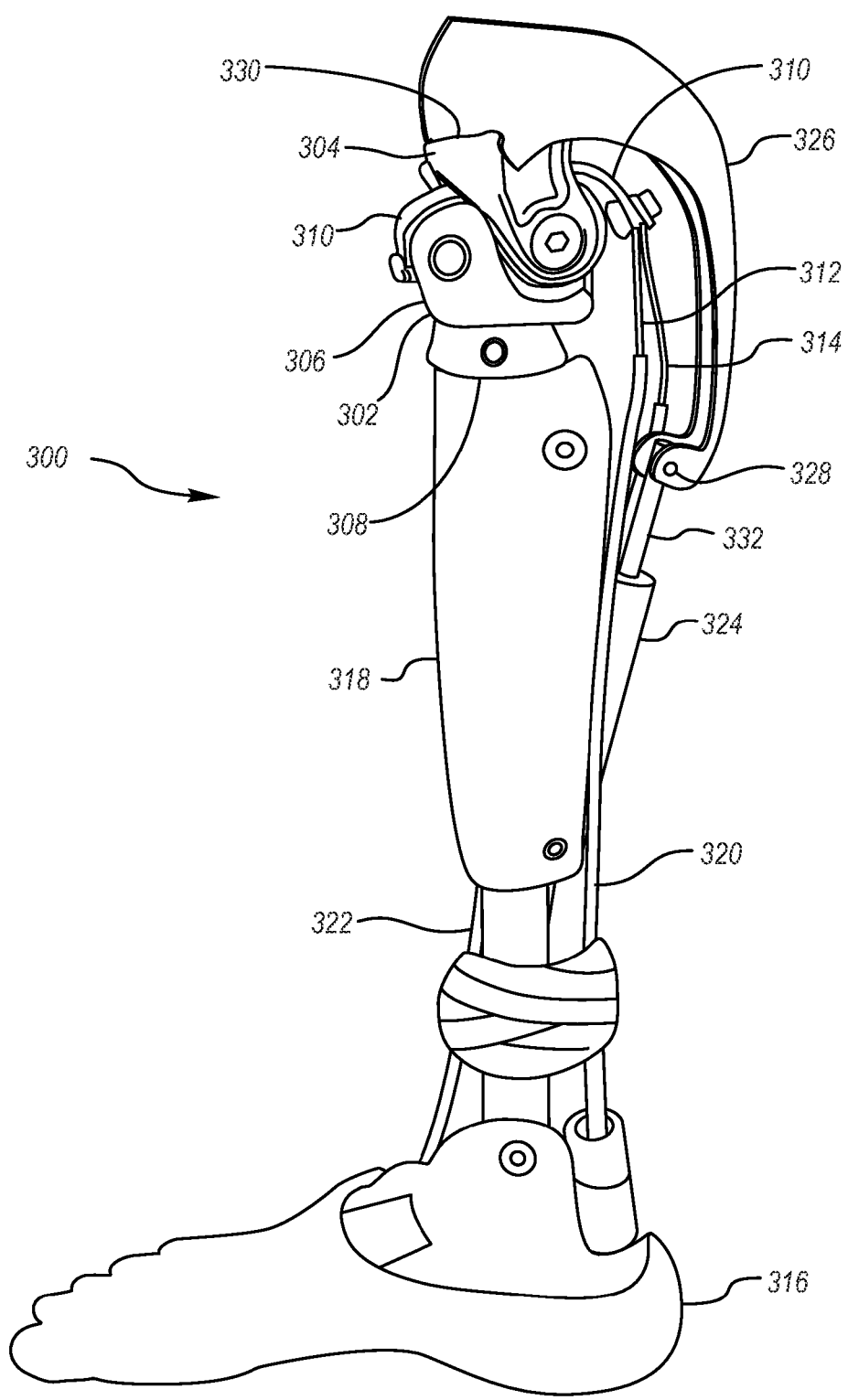
FIG. 8 is a side view of some components of another implementation of a conditional braking knee.

Referring now to FIG. 8, in implementations a conditional braking knee (CBK) 300 may be formed by modifying a conventional braking knee 302. In this specific implementation the conventional braking knee 302 was part of a prosthetic leg and the knee portion has a braking element to brake the conventional braking knee 302 under a load. In order to retrofit the conventional braking knee 302 to add the dorsiflexion and plantarflexion braking mechanisms, the conventional braking knee 302 was severed from the leg portion 318 and the conventional braking knee 302 was flipped upside down, then reattached to the leg portion 318 at the lower attachment point 308. This was done to configure the braking mechanism of the conventional braking knee 302 to be activated upon receiving a downward force instead of an upward force. The braking member 310 was then coupled to the conventional braking knee 302, between upper portion 304 and lower portion 306 of the conventional braking knee 302, and the braking member 310 was in turn coupled to the dorsiflexion coupler 312 and the plantarflexion coupler 314, so that in plantarflexion of the prosthetic foot 316 the braking member 310 would provide a downward force within the conventional braking knee 302 to brake it, and in dorsiflexion of the prosthetic foot 316 the braking member 310 would also provide a downward force within the conventional braking knee 302 to brake it.

Although in this implementation the conventional braking knee 302 was severed from the leg portion 318 and flipped upside down, in other implementations the dorsiflexion and plantarflexion couplers 312, 314 could be re-routed so that they pull upward on the braking member 310, instead of downward, or they could otherwise be configured to provide an upward force (such as with rigid pushrods) so that the conventional braking knee 302 does not have to be severed from the leg portion 318 and turned upside down.

Although the implementation in FIG. 8 is a retrofitting of a conventional braking knee 302, leg portion 318 and prosthetic foot 316, in implementations the elements of the CBK 300 of FIG. 2 could be formed during a manufacturing and assembly stage instead of making modifications to already-manufactured and/or already-assembled conventional devices. In methods of actually retrofitting an existing conventional braking knee 302 in the manner shown in FIG. 2, in any instances in which one or more members is severed and reattached, the reattachment may be done, for instance, with epoxy, a glue, screws, a friction fit, and any other known or hereafter discovered attachment technique.

In the implementation of FIG. 8 the dorsiflexion coupler 312 movably resides within a dorsiflexion sheath 320 from a location proximate the prosthetic foot 316 to a location proximate the braking member 310. Likewise, the plantarflexion coupler 314 movably resides within a plantarflexion sheath 322 from a location proximate the prosthetic foot 316 to a location proximate the braking member 310. In implementations the sheaths 320, 322 may be omitted.

Referring still to FIG. 8, an extension member 324 is coupled to the leg portion 318 and a piston 332 couples the extension member 324 to an extension coupler 326. The extension coupler 326 is in turn coupled to the conventional braking knee 302 at an upper attachment point 330. The extension member 324, when it extends the piston 332, thus results in moving the conventional braking knee 302 to the configuration shown in FIG. 8—in other words it places the leg portion 318 in a position such that it is generally collinear with the residual limb of a user, or straightens the leg out, such as in a standing position. In implementations the extension member 324 could be configured to be reversible, such as for instance to move the leg portion 318, when desired, to a bended configuration or, in other words, to a configuration wherein the leg portion 318 is substantially not collinear with (or in some instances is orthogonal to), the residual limb of a user, such as when the user is in a sitting position, a squatting position, or some other position between sitting and standing or squatting and standing.

In various implementations, the extension member 324 may be a replaceable module that may be removed and replaced with another type of extension member 324. By non-limiting example, in implementations a piston 332 of the extension member 324 may be removable from an axle joint 328 of the extension coupler 326 and/or may be otherwise removable from the leg portion 318 so as to replace the extension member 324 with another extension member 324, either of the same type or of another type. Different types of extension members 324 may include, by non-limiting example, one or more or all of the following mechanisms: springs, pneumatics, hydraulics, a motor, and so forth. A motorized version may use a motor and gears of any type and configuration to transmit rotation of the motor shaft into interaction with the extension coupler 326. In implementations, for example, a motor may utilize transverse gears to convert the rotation of the motor shaft into a movement of the extension coupler 326 as desired. In implementations a piston 332 may be used with any of a spring version, a pneumatic version, a hydraulic version, or a motorized version of an extension member 324. In implementations of a motorized version the piston may be coupled to the motor, such as through gears, and coupled to the axle joint 328, or in implementations a portion of the motor may be coupled directly to the axle joint 328 without the use of a piston 332, or the motor may be otherwise coupled to the axle joint 328.

Figure 9:
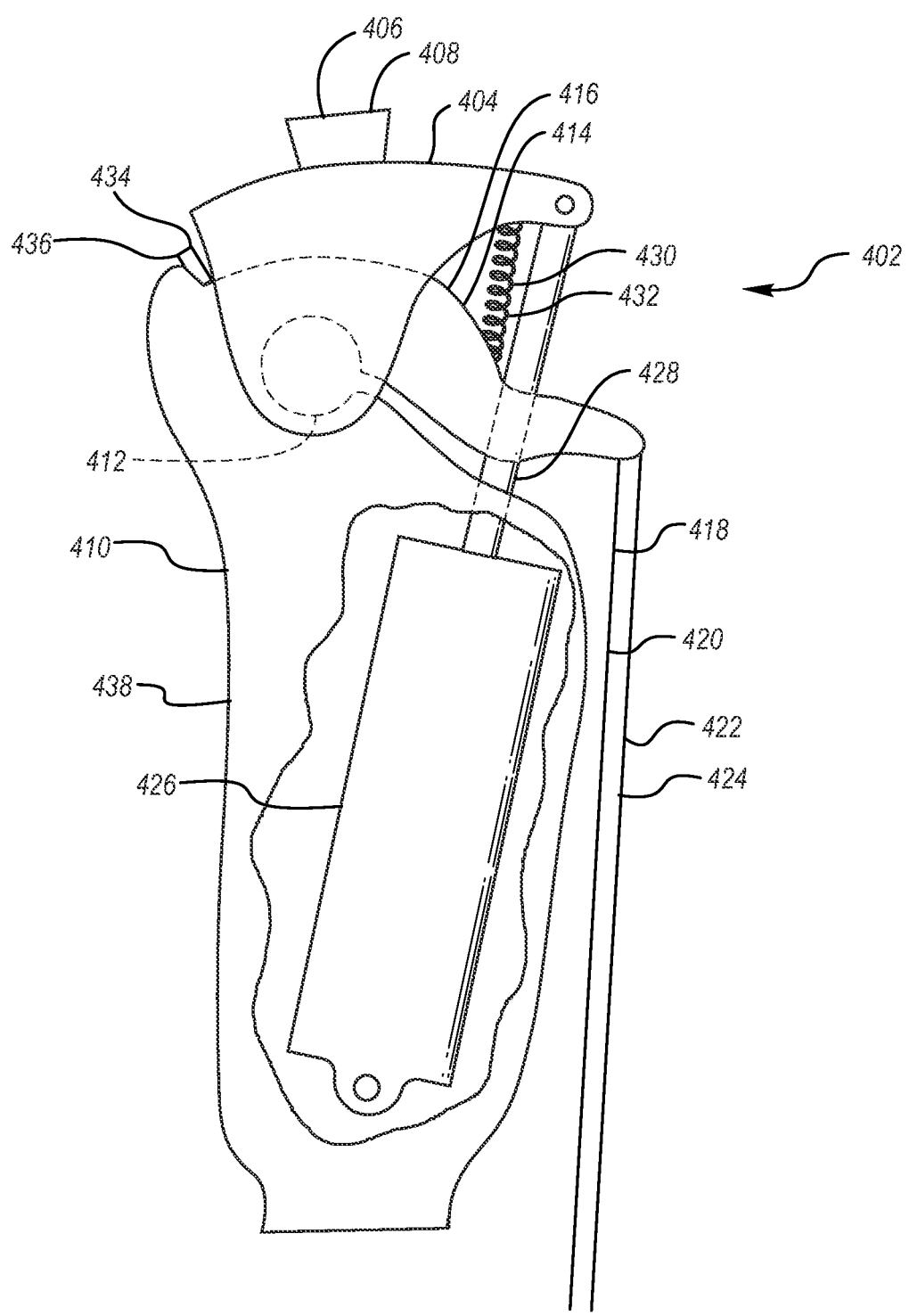
FIG. 9 is a side, partial see-through view of some components of another implementation of a conditional braking knee.

Referring now to FIG. 9, in implementations a conditional braking knee (CBK) 402 includes an upper member 404 coupled to a lower member 410 using an axle 412, the axle 412 allowing the upper member 404 and lower member 410 to rotate with respect to one another in at least one plane of rotation. The upper member 404 includes a first coupler 406 by which the upper member 404 may be coupled to the residual limb of a user such as, by non-limiting example, by coupling to a prosthetic socket which in turn is coupled to a residual limb of a user. In implementations the first coupler 406 comprises an endoskeletal pyramid 408.

In implementations the CBK 402 includes a braking member 414 configured to prevent rotation of the axle 412 relative to either or both of the upper member 404 and lower member 410 in response to an input, a mechanical movement or force, insertion of a locking mechanism, or the like. In implementations the braking member 414 is integral to the lower member 410 and comprises an arm 416 that is configured for contact with the axle 412 and which, when pushed down tightens on the axle 412 thereby hindering and/or preventing rotation of the axle 412 to effectively "brake" the CBK 402. In other implementations the braking member 414 could be integral to the upper member 404, or a separate component that is coupled to the axle 412, and so forth.

In implementations the braking member 414 may perform a braking function in response to a force that results in increased friction between the braking member 414 and the axle 412. By non-limiting example, in the implementation of FIG. 9 a prosthetic foot may be coupled to the lower member 410 and two couplers may couple the prosthetic foot to the braking member 414: a plantarflexion coupler 418 and a dorsiflexion coupler 422. The plantarflexion coupler 418 is configured to cause the braking member 414 to perform a braking function in response to plantarflexion of the prosthetic foot. The dorsiflexion coupler 422 is configured to perform a braking function in response to dorsiflexion of the prosthetic foot. In the implementation shown in FIG. 9 this is accomplished by the plantarflexion coupler 418 having or being a flexible cable 420 and the dorsiflexion coupler 422 having or being a flexible cable 424 such as, by non-limiting example, braided metal cables, such that a dorsiflexion or plantarflexion of the prosthetic foot results in a downward pull of one of the flexible cables 422, 424, thus activating the braking member 414, this in turn causing increased friction between the axle 412 and the braking member 414 to hinder and/or disallow rotation of the axle 412 relative to the lower member 410. Enough downward force will prevent rotation of the axle 412 relative to the lower member 410 and will thus effectively "brake" or "lock" the CBK 402 to prevent rotation.

Although the above-described implementation of the CBK 402 utilizes mechanical elements, such as metal cables, for the plantarflexion coupler 418 and dorsiflexion coupler 422, in other implementations the plantarflexion coupler 418 and/or the dorsiflexion coupler 422 could be, by non-limiting example, electrical wires that couple to the braking member 414, the electrical wires configured to transmit a signal to the braking member 414 in response to dorsiflexion or plantarflexion of the prosthetic foot and activate the braking member 414 through other mechanical and/or motorized means to apply a braking force to the axle 412. In such implementations an additional backup braking mechanism may or may not be utilized, such as for instance to provide braking in the instance that a power source involved in the electrical communication fails or drops below some necessary charge to function properly. In implementations the braking force need not be directly applied to the axle 412 but may be applied, by non-limiting example, to a portion of the lower member 410 and a portion of the upper member 404 to prevent them from moving with respect to one another, and so forth. In implementations the braking member 414 is comprised of some element other than an arm 416 configured to have a high friction with the axle 412.

Referring still to FIG. 9, in implementations the CBK 402 includes an extension member 426 coupled to the lower member 410 and to the upper member 404 and configured to extend, or assist in extending, the lower member 410 relative to a user's residual limb (such as to straighten the lower member 410 so that it is generally aligned or generally collinear with the residual limb of the user). In implementations the extension member 426 may comprise one or more or all of the following: springs; a pneumatic controlled piston 428; a hydraulic mechanism; a motor; and the like. In implementations the extension member 426 may be interchangeable so that, for instance, one of the above implementations may be changed out for another one in any given CBK 402. In implementations the extension member 426 may be used for only one, or for both, of: extension during the swing phase of normal walking, and; extension during a standing process whereby a user stands up from a sitting position.

In motorized versions of an extension member 426 the extension member 426 may not be needed during a normal swing phase during normal walking so that battery life may be preserved and/or so that a requisite battery size may be reduced. For example, electrical power may be used only during rising from a chair or elevating oneself upstairs. In such an implementation electrical power may not be needed for normal leg extension during a standing position or during a swinging motion during ambulation. In implementations the motorized power may be supplemented with other mechanisms, such as a spring, pneumatics, hydraulics or the like, to assist in extending the knee during a standing position and/or during normal ambulation swinging. In implementations the extension member 426 may comprise one or more of the components of a right angle drill, such as those marketed under the trade name DEWALT by DEWALT Industrial Tool Co. of Baltimore, Md. In implementations of a motorized extension member 426 the extension member 426 may include one or more or all of the following features: the motor may be reversible; the motor may have high torque; the motor may have a variable speed; the motor may run on a lithium ion battery; and the like.

Referring again to FIG. 9, in implementations the CBK 402 further includes a resistance member 430 configured to perform one or more or all of the following functions: slow down an extension of the extension member 426; resist a full opening of the upper and lower members 404, 410 into a straight-leg configuration (such that the lower member 410 is roughly collinear with the residual limb), and; resist the lower member 410 being rotated to a bended configuration relative to the residual limb (such that the lower member 410 is not collinear with the residual limb). In implementations the resistance member 430 may perform one or more or all of the above functions increasingly, or with increased force, as the lower member 410 approaches a fully extended or fully bended configuration, as the case may be, relative to the residual limb. In implementations the resistance member 430 is a deceleration compression spring 432.

Referring still to FIG. 9, in implementations the CBK 402 comprises a bumper 434 configured to resist the lower member 410 rotating past a specified rotation relative to the upper member 404. The bumper 434 in implementations may comprise, by non-limiting example, an elastic polymer or rubber material 436. The bumper 434 may also be configured in such a way to cause the offloading of the braking system in the last 5 degrees of extension to allow for a free swing motion at terminal stance.

In implementations the lower member 410 may comprise a frame or housing 438 within which to at least partially house a portion of the extension member 426. The lower member 410 (and upper member 404) in implementations may comprise a composite material. In implementations the lower member 410 may be permanently fixed to a prosthetic foot, while in other implementations the lower member 410 may have a foot coupler configured to allow a prosthetic foot to be releasably coupled to and removed from the lower member 410. For example, the lower member 410 may be configured to permanently or removably receive a pylon or a coupler (such as, by non-limiting example, an endoskeletal pyramid) of a prosthetic foot.

The following details may be applied to any conditional braking knee, according to any of the implementations disclosed herein or according to any implementation not disclosed herein.

In implementations a conditional braking knee, in implementing plantarflexion and dorsiflexion braking mechanisms, may implement a conditional mechanical lock at any angle (i.e., any angle of the residual limb relative to the lower portion or lower leg of the prosthetic leg, or in other words any angle of the upper member relative to the lower member, etc.). In implementations a conditional braking knee may include a switch and/or sensor that is configured to activate a motor of the conditional braking knee in response to some event. By non-limiting example, in implementations a switch may be located above a socket and, when a user is sitting down and leans forward, such as to prepare to stand up, the switch may be activated either by being pushed by the user's body (such as the user's stomach or abdomen)—or the switch may include a sensor that senses that the person's upper body is tipped forward in preparation for standing—and the motor may, in response, be activated to straighten the artificial knee such as to assist the user in standing up.

In implementations a conditional braking knee may also use computerized braking or other computerized mechanisms. In implementations a conditional braking knee may provide decreased anterior migration of a prosthetic knee, relative to a conventional prosthetic knee, during an upward climbing motion, such as during stair climbing. In implementations the braking member of a conditional braking knee may be activated manually, such as using cables, springs, or the like. In implementations the braking member may be activated using electromagnetics that are triggered magnetically or electronically, wired or wireless, etc. In implementations the braking member may utilize strain gauges, myoelectrics, pneumatics, hydraulics, input from a gyroscope that measures spatial changes, thermal changes, and the like.

In implementations the components of a conditional braking knee may be designed to be incorporated into a conventional braking knee. In implementations elements of a conditional braking knee could be used to lock one, all, or any bar (or associated center of rotation) of a multiple bar knee, such as a four bar, five bar, or seven bar knee, or the like. In implementations one or more braking mechanisms of a conditional braking knee may be refined so that it is gradual, allowing a patient to feel its tolerances throughout the gait cycle, thus increasing proprioception while adding the prosthetic swing characteristics close to those offered by hydraulics and pneumatics.

Implementations of conditional braking knees may include one, all, or any of the elements, features, limitations, structures, mechanisms, methods, and the like, disclosed in any of the following references, the disclosures of each of which are incorporated entirely herein by reference: U.S. Pat. No. 7,468,079 to Collier, issued Dec. 23, 2008; U.S. Pat. No. 7,025,792 to Collier, issued Apr. 11, 2006; U.S. Pat. No. D398058 to Collier, issued Sep. 8, 1998; U.S. Pat. No. 5,800,570 to Collier, issued Sep. 1, 1998; U.S. Pat. No. 5,545,234 to Collier, Jr., issued Aug. 13, 1996, and; WIPO Pub. No. WO1997033540A1 to Collier, published Sep. 18, 1997.

In implementations a conditional braking knee may be used in orthotic joints and not just artificial limb joints. In implementations the conditional braking knee, or elements, components, sub-element and sub-components of a conditional braking knee may be used in industries other than artificial limb industries, such as in any application wherein conditional braking as described herein would be useful.

In some implementations of conventional braking knees there is a critical flexion angle that, when exceeded, causes the weight activated knee to no longer be effective. This sometimes occurs, by non-limiting example, when a user is climbing stairs using a prosthetic knee. In this circumstance, when the braking knee has reached a critical flexion angle, weight loaded onto the knee does not cause the braking knee to brake, or does not cause the braking knee to brake effectively, and/or is instead translated into further knee rotation. This, in some instances, in turn causes inefficiency and wasted energy because a user then has to overcome the additional rotation of the prosthetic knee before bringing the knee back to a fully-open position.

In implementations a conditional braking knee results in a conservation of energy, or less energy loss, relative to a conventional braking knee, because the braking member is effective to brake the prosthetic knee to prevent further rotation of the knee even if the prosthetic knee has already reached what would have been a critical flexion angle. Additionally, in implementations the conditional braking knee prevents the prosthetic knee from reaching the critical flexion angle in the first place because a user can brake the knee at a desired angle using the braking member and/or the dorsiflexion and/or the plantarflexion coupler(s). Thus, in implementations a conditional braking knee is effective at an angle, and beyond those angles, at which a conventional braking knee loses (or has greatly reduced) effectiveness.

In implementations of a conditional braking knee the conditional braking from the braking member and the primary braking that is native to the braking knee (for instance that is integral to a conventional or weight-activated braking knee) reinforce one another. By non-limiting example, in implementations the secondary (plantarflexion or dorsiflexion) braking mechanism essentially reactivates the primary braking that is native to the braking knee after it has exceeded its critical flexion angle, thus making the knee lock. This rigidity in the knee then transfers forward motion into the foot (instead of rotation of the knee), thus pulling the secondary brake harder as the user rolls onto the toe and the heel leaves the ground. In implementations the secondary braking and primary braking mechanisms reinforce one another proportionally and/or exponentially.

In some implementations a tertiary braking mechanism may be implemented relying on a flexion angle of a socket relative to the braking knee or upper member. By non-limiting example, in implementations the dorsiflexion and/or plantarflexion coupler may work in concert with the position of the tertiary braking member and/or in concert with a flexion angle of a socket relative to the braking knee or upper member. For example, in implementations a user may be sitting down with the prosthetic foot flat on the ground, the ankle neutral and no load on the toe. In such a scenario there would be little or no braking force on the prosthetic knee. However, a similar positioning of the foot during ambulation may result in dorsiflexion and, therefore, braking due to the dorsiflexion coupler. This mechanism may be useful for instance when a user is exiting a chair, where there is an excessive flexion angle in the socket and a load on the toe, and when climbing stairs. In implementations a motorized element may be implemented to extend the knee when both of these conditions (excessive flexion angle in the socket and load on the toe) are met. This motorized element may be any disclosed in this document. In implementations a brim switch may be included, located at the proximal anterior and/or posterior aspect of the socket, as a safety measure.

In implementations the secondary braking mechanisms, using the dorsiflexion coupler and/or plantarflexion coupler and braking member, activate a brake in response to a relationship of the foot relative to the knee. In implementations the tertiary braking mechanism, using the flexion angle of the socket, activates a brake in response to a relationship of the socket to the knee. Although in the implementations shown the dorsiflexion coupler and plantarflexion coupler are both tensile devices, i.e., the braking member is activated in response to a tensile force in either or both, in other implementations either or both of the dorsiflexion coupler and plantarflexion coupler could be compression devices. For instance one or both could be rigid rods, whereby plantarflexion and/or dorsiflexion of the foot results in an upwards compressive force on the braking member, the braking member configured to translate this upwards compressive force into a braking of the knee. In implementations such rigid rods, or pushrods, could be located in a posterior, anterior, or combination of posterior and anterior position, relative to the foot and/or knee. In implementations a pylon of the prosthesis may be vertically telescopic, selectively decreasing and increasing in vertical height, to accomplish this compression and the later expansion.

In implementations an electrically-powered braking mechanism may be utilized in conjunction with a backup manual braking mechanism. For example, for most braking knees a motion is needed (under a load) to cause a friction between one or more elements of the braking knee (for instance by placing high-friction components in contact with one another) in order to provide the braking of the knee. In implementations wherein an electrically powered braking mechanism is used, a solenoid or other device or mechanism may be used to prevent this motion and/or contact, and thus to prevent the resultant friction and normal braking mechanism, while braking the knee in an alternative fashion using electrical power. If the electrical power fails or runs low, the solenoid may cease operating or otherwise change its configuration, thus allowing the aforementioned motion and/or contact, allowing the friction and allowing the manual braking to once again take place. In this way the conditional braking knee may be safe even if the power to the electrically powered brake fails or runs low.

In implementations an electrical motor could be configured to be coupled to the rotational axis of the braking knee to cause the socket and knee to change positions relative to one another (or the socket and lower member of the knee, or the socket and leg portion below the knee). In implementations such a coupling and/or the motor itself may include one or more or all of the following: gears; pulleys; chains; belts; solenoids; electromagnetics; hydraulics; pneumatics; elastics; and the like. In implementations of a myoelectric triggered braking mechanism electrical power may be used only for extension of the knee and manual braking may be used for prevention of flexion of the knee.

In implementations body power may be used to power one or more elements of a CBK. For example, power generated from the movement of one joint relative to another, or reciprocal expansion/contraction of muscles on either side of a joint during limb movement, and the like, may be captured and/or otherwise used to provide power to a CBK, either manual "real time" power or to store power mechanically, electrically, or in any other way. Such mechanisms as are used with orthotic devices, such as orthotic hip devices, may be used and/or retrofitted to be used with a CBK for this purpose.

In implementations of the above-referenced braking mechanisms, such as the primary braking mechanism of the braking knee, the braking mechanism utilizing the plantarflexion coupler, the braking mechanism utilizing the dorsiflexion coupler and/or the braking mechanism utilizing the tertiary braking mechanism (relying on flexion angle of the socket), one or more or each of the braking mechanisms may have a separate brake. In other implementations each braking mechanism will operate in conjunction with a single brake. In implementations there may be multiple brakes, but not one brake for each braking mechanism. In implementations of a multi-bar knee each bar may have its own brake.

Implementations of conditional braking knees may be made of conventional materials used to make goods similar to these in the art, such as, by non-limiting example, metals, composites, polymers, ceramics, and the like. Those of ordinary skill in the art will readily be able to select appropriate materials and manufacture these products from the disclosures provided herein.

In places where the description above refers to particular implementations of conditional braking knees and related methods and implementing components, sub-components, methods and sub-methods, it should be readily apparent that a number of modifications may be made without departing from the spirit thereof and that these implementations, implementing components, sub-components, methods and sub-methods may be applied to other conditional braking knees and related methods.

What is claimed is:

1. A conditional braking knee, comprising:
    an upper member configured to couple to a prosthetic socket;
    a braking member coupled to the upper member through a first axle, the first axle at least partially housed within a clamping member of the braking member, the braking member comprising a dorsiflexion attachment point and a plantarflexion attachment point directly adjacent to the first axle;
    a lower member directly and rotatably coupled to the braking member through a second axle and configured to rotate with respect to the upper member; and
    a dorsiflexion coupler coupled to the dorsiflexion attachment point and a plantarflexion coupler coupled to the plantarflexion attachment point of the braking member both the dorsiflexion coupler and the plantarflexion coupler configured to couple to a prosthetic foot;
    wherein the dorsiflexion attachment point and the plantarflexion attachment point are located posterior relative to the first axle and the second axle;
    wherein the braking member is configured to prevent the rotation of the braking member relative to the upper member about the first axle at and beyond a critical flexion angle of the upper member relative to the lower member in response to a flexion of the prosthetic foot communicated to the braking member through one of the dorsiflexion coupler and the plantarflexion coupler; and
    wherein the upper member is rotatable relative to the lower member through the first axle.

2. The conditional braking knee of claim 1, wherein the conditional braking knee further comprises the prosthetic foot and the prosthetic foot is coupled to the lower member and to the dorsiflexion coupler and to the plantarflexion coupler.

3. The conditional braking knee of claim 2, wherein the plantarflexion coupler is coupled to a plantarflexion coupler receiver of the prosthetic foot and the dorsiflexion coupler is coupled to a dorsiflexion coupler receiver of the prosthetic foot.

4. A conditional braking knee, comprising:
    an upper member configured to couple to a prosthetic socket;
    a clamping member rotatably coupled to the upper member with a first axle, the first axle at least partially housed within the clamping member, the clamping member comprising a dorsiflexion attachment point and a plantarflexion attachment point directly adjacent to the first axle;
    a lower member directly and rotatably coupled to the clamping member with a second axle;
    two flexion couplers coupled to the dorsiflexion attachment point and the plantarflexion attachment point of the clamping member, respectively; and
    a prosthetic foot coupled to the two flexion couplers;
    wherein the dorsiflexion attachment point and the plantarflexion attachment point are located posterior relative to the first axle and the second axle;
    wherein the clamping member is configured to prevent the rotation of the clamping member relative to the upper member about the first axle at and beyond a critical flexion angle of the upper member relative to the lower member in response to a flexion of the prosthetic foot by clamping on the first axle; and
    wherein the upper member is rotatable relative to the lower member through the first axle.

5. The conditional braking knee of claim 4, wherein the two flexion couplers comprise a plantarflexion coupler configured to apply a force to the clamping member in response to a plantarflexion of the prosthetic foot and a dorsiflexion coupler configured to apply a force to the clamping member in response to a dorsiflexion of the prosthetic foot.

6. The conditional braking knee of claim 5, wherein the force applied by each of the plantarflexion coupler and the dorsiflexion coupler is a downward force.

7. The conditional braking knee of claim 5 wherein the plantarflexion coupler is coupled to a plantarflexion coupler receiver of the prosthetic foot and the dorsiflexion coupler is coupled to a dorsiflexion coupler receiver of the prosthetic foot.

8. The conditional braking knee of claim 4, wherein the two flexion couplers comprise flexible cables.

9. The conditional braking knee of claim 4, wherein the upper member is rotatable relative to the lower member through the second axle.

10. A conditional braking knee, comprising:
    an upper member configured to couple to a prosthetic socket;
    a clamping member rotatably coupled to the upper member with a first axle, the first axle at least partially housed within the clamping member, the clamping member comprising a dorsiflexion attachment point and a plantarflexion attachment point directly adjacent to the first axle;
    a lower member directly and rotatably coupled to the clamping member with a second axle;
    a plantarflexion coupler coupled to the plantarflexion attachment point of the clamping member;
    a dorsiflexion coupler coupled to the dorsiflexion attachment point of the clamping member; and
    a prosthetic foot coupled to the plantarflexion coupler and to the dorsiflexion coupler;

wherein the dorsiflexion attachment point and the plantarflexion attachment point are located posterior relative to the first axle and the second axle;

wherein the plantarflexion coupler is configured to apply a first force to the clamping member in response to a plantarflexion of the prosthetic foot and the clamping member is configured to prevent the rotation of the clamping member relative to the upper member about the first axle at and beyond a critical flexion angle of the upper member relative to the lower member in response to the first force by clamping on the first axle;

wherein the dorsiflexion coupler is configured to apply a second force to the clamping member in response to a dorsiflexion of the prosthetic foot and the clamping member is configured to prevent the rotation of the upper member relative to the lower member about the first axle in response to the second force by clamping on the first axle; and wherein the upper member is rotatable relative to the lower member through the first axle.

11. The conditional braking knee of claim 10, wherein the upper member is rotatable relative to the lower member through the second axle.

12. The conditional braking knee of claim 10, wherein the plantarflexion coupler is coupled to a plantarflexion coupler receiver of the prosthetic foot and the dorsiflexion coupler is coupled to a dorsiflexion coupler receiver of the prosthetic foot.

\* \* \* \* \*